(12) United States Patent
Stammler et al.

(10) Patent No.: US 6,384,272 B2
(45) Date of Patent: May 7, 2002

(54) METHOD FOR PREPARING ASPARTYLCYCLOHEXYLA LANINAMIDE

(75) Inventors: Robert Stammler; Christophe Daubie, both of Paris; Michel Lavigne, Chilly Mazarin, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/729,011

(22) Filed: Dec. 4, 2000

Related U.S. Application Data

(63) Continuation of application No. PCT/FR99/01300, filed on Jun. 3, 1999.
(60) Provisional application No. 60/104,417, filed on Oct. 15, 1998.

(30) Foreign Application Priority Data

Jun. 5, 1998  (FR) ............................................. 98 07069

(51) Int. Cl.$^7$ ...................... C07C 229/00; C07C 315/00
(52) U.S. Cl. ........................................ 562/443; 562/507
(58) Field of Search .................................. 562/443, 507

(56) References Cited

U.S. PATENT DOCUMENTS 5,340,802 A    8/1994    Shiosaki

FOREIGN PATENT DOCUMENTS

WO    WO 98/46629    10/1998

*Primary Examiner*—Alan Siegel
(74) *Attorney, Agent, or Firm*—Irving Newman

(57) ABSTRACT

Disclosure is a method for preparing α-aspartyl-β-cyclohexylalaninamide, comprising carrying out a first step of amide formation of an α-aspartyl phenylamine ester of general formula (II)

(II)

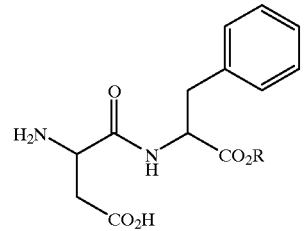

wherein: R is a $C_1$–$C_4$ alkyl radical, and then performing a catalytic hydrogenation of the resulting α-aspartyl phenylalaninamide ammonium salt, optionally released previously from its salt, and optionally transforming it into an addition acis salt.

8 Claims, No Drawings

METHOD FOR PREPARING ASPARTYLCYCLOHEXYLA LANINAMIDE

CROSS-REFERENCE TO RELATED APPLICATIONS

This application is a continuation of International Application No. PCT/FR99/01300 filed Jun. 3, 1999, which application, in turn, claims priority from U.S. Provisional Patent Application No. 60/104,417 filed Oct. 15, 1998 and French Patent Application No. 98/07069, filed Jun. 5, 1998.

FIELD OF THE INVENTION

The present invention relates to an improved method for preparing (α-aspartyl)-β-cyclohexylalaninamide from an ester of (α-aspartyl)phenylalanine.

BACKGROUND OF THE INVENTION (α-Aspartyl)phenylalaninamide is usually prepared by peptide coupling of derivatives of aspartic acid and of phenylalaninamide. These couplings require protective operations to be carried out on the aspartic acid, and the phenylalaninamide has to be prepared from phenylalanine. After peptide coupling, amine and acid deprotective operations are needed to gain access to (α-aspartyl) phenylalaninamide, thus rendering its synthesis lengthy, inefficient and expensive [J. Org. Chem., 40, 2495 (1975); WO 9006937;DD 209 191; DE 2 245 459; EP 149 582].

Patent Application WO 95/10295 has disclosed the preparation of pseudotetrapeptide derivatives of general formula:

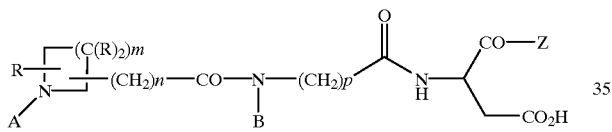

in which in particular Z represents:

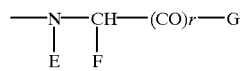

for which E is in particular hydrogen, F is in particular cycloalkylalkyl, r can be 1 and G can form an $NR_1R_2$ group.

These derivatives, which are active in the cardiovascular field, are prepared via aspartic derivatives, such as, for example, the aspartic derivative of general formula:

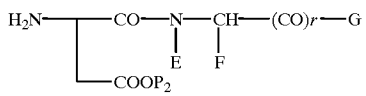

However, the process is fairly lengthy and expensive, since it involves starting materials, such as cyclohexylalanine and the monobenzyl ester of benzyloxycarbonylaspartic acid, which are not commercially available, in particular on an industrial scale, which starting materials have to be protected beforehand before they are employed in the process. Thus, the industrial preparation of the biologically active product is extremely laborious.

Patent Application EP 405 506 has disclosed the preparation of (α-aspartyl)cyclohexylalaninamide by catalytic hydrogenation of (α-aspartyl)phenyl-alaninamide. However, (α-aspartyl)phenylalaninamide prepared by conventional methods could not make it possible to obtain an overall improvement in the method.

SUMMARY OF THE INVENTION

It has now been found, and it is this which forms the subject-matter of the present invention, that it is possible to prepare the ammonium salt of (α-aspartyl) phenylalaninamide of formula:

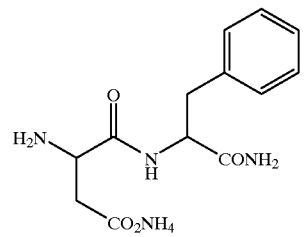

(I)

directly from an ester of (α-aspartyl)phenylalanine of general formula:

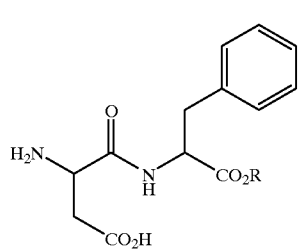

(II)

in which R is an alkyl radical comprising 1 to 4 carbon atoms, and that it is possible, for this reason, to prepare (α-aspartyl)-β-cyclohexylalaninamide or its salt in only 2 stages.

DETAILED DESCRIPTION OF THE INVENTION

According to the invention, the ammonium salt of (α-aspartyl)phenylalaninamide is prepared by amidation of the ester of (α-aspartyl)phenylalanine of general formula (II) and then, in a second stage, (α-aspartyl)-β-cyclohexylalaninamide is obtained by catalytic hydrogenation of the product obtained, optionally released beforehand from its salt (optionally in situ).

According to a preferred form of the invention, the method is carried out on the ester of ((L)-α-aspartyl)-(L)-phenylalanine in order to prepare ((L)-α-aspartyl)-(L)-phenylalaninamide and then ((L)-α-aspartyl)-(L)-β-cyclohexylalaninamide.

Also according to a preferred form, the invention can be carried out starting from the methyl ester of (α-aspartyl) phenylalanine.

According to the invention, the amidation reaction is carried out by reaction with liquid ammonia at a temperature of between −40 and 20° C. It can optionally be carried out in the presence of a cosolvent, such as water, an alcohol (methanol, ethanol, isopropanol or ethylene glycol) or acetonitrile.

When it is desired to release the product from its salt, in order to obtain ((L)-(α-aspartyl)-(L)-phenylalaninamide as an intermediate, the ammonium salt obtained above can either be directly heated for 12 to 16 hours at a temperature of between 30 and 40° C. while flushing with nitrogen and optionally under reduced pressure or can be treated in an aqueous acidic medium as described below in the examples, in particular with acids as described below.

When it is desired to release the product from its salt and to obtain an acid salt, the ammonium salt is treated in an acidic medium, according to the usual methods which do not detrimentally affect the remainder of the molecule, as described below in the examples, in particular, and without implied limitation, with acids such as hydrochloric acid, tartaric acid, acetic acid, oxalic acid, lactic acid, citric acid or mandelic acid.

The catalytic hydrogenation stage is carried out at a temperature of between 20 and 60° C. (preferably at 40° C.) under a hydrogen pressure of 1 to 8 bar (preferably 4 bar) in an aqueous hydrochloric acid medium or in an acetic acid medium in the presence of platinum and optionally in the presence of another organic acid, such as, for example, trifluoroacetic acid, trichloroacetic acid, oxalic acid, malonic acid, citric acid, tartaric acid, malic acid, formic acid or lactic acid.

The derivatives obtained by the method according to the invention can optionally be converted to addition salts with acids.

Mention may be made, among industrially advantageous salts, of the hydrochloride, hydrobromide, tartrate, acetate, oxalate, lactate, citrate, mandelate or trifluoroacetate.

The method according to the invention is particularly advantageous owing to the fact that it opens the route to the preparation of (α-aspartyl)-β-cyclohexylalaninamide in only 2 stages and also owing to the fact that it makes it possible to prepare the intermediate amide of formula (I) in a single stage from a starting material which is readily accessible industrially: aspartame.

The (α-aspartyl)-β-cyclohexylalaninamide thus obtained can be purified according to the usual methods, such as chromatography or crystallization.

(α-Aspartyl)-β-cyclohexylalaninamide can be employed in the preparation of pseudotetrapeptide derivatives by carrying out the preparation according to the method disclosed in International Application WO 95/10295.

The following examples, given without implied limitation, illustrate the present invention.

EXAMPLE 1

500 cm$^3$ of liquid ammonia are charged to a 2 liter jacketed reactor cooled by circulation at −40° C. and then 250 g of methyl ester of ((L)-α-aspartyl)-(L)-phenylalanine are added over 30 minutes with stirring. A colourless solution is obtained, which solution is stirred for a further 1 hour at −40° C. Circulation in the jacket is halted and the mixture is allowed to warm up and to degas with stirring. The solution becomes concentrated, thickens and becomes viscous over 2 hours, stirring is halted and the mixture is allowed to degas. The mixture crystallizes in the form of a foam. Degassing is completed under reduced pressure (4 hours at 5.3 kPa). After having purged with nitrogen, 239 g of the ammonium salt of ((L)-α-aspartyl)-(L)-phenylalaninamide are obtained with a yield of 95%.

$^1$H NMR spectrum, d$_6$-DMSO, T=300° K., δ in ppm (300 MHz): 2.15 and 2.42 (each 1H, respectively dd, J=9 and 16 Hz, and dd, J=5 and 16 Hz, COCH$_2$), 2.86 and 3.07 (each 1H, respectively dd, J=9 and 14 Hz, and dd, J=4 and 14 Hz, PhCH$_2$), 3.54 (1H, q, J=4 and 9 Hz, NCH), 4.40 (1H, m, NCH), 7.10 (1H, s, ½ CONH$_2$), 7.25 (5H, m, phenyl), 7.74 (1H, s, ½CONH$_2$), 8.60 (1H, broad s, NH).

Infrared spectrum, KBr pellet, cm$^{-1}$: broad band from 3600 to 2000, bonded ν N—H, including ν NH$_4^+$ with maxima at approximately 3388+3284+3190, ν N—H of the amides, 3086+3063+3029, ν C—H of the monosubstituted benzene; bands at approximately 1673, ν C═O of the primary amide, 1637 mainly ν C═O of the secondary amide, 1567 mainly ν$_{as}$ C═O of COO$^-$+δ NH of the secondary amide, 1496+1454 C═C monosubstituted benzene nucleus, 1444 to deformation of CH$_2$, 1393 ν$_s$ C═O of COO$^-$+δ NH$_4^+$, 1031 monosubstituted benzene nucleus, 750 γ C—H of the monosubstituted benzene nucleus, 698 deformation of the monosubstituted benzene nucleus.

500 cm$^3$ of water and 250 cm$^3$ of 6N hydrochloric acid are charged to a stirred 2 liter jacketed reactor cooled by circulation at 10° C., 239 g of the ammonium salt of ((L)-α-aspartyl)-(L)-phenylalaninamide prepared above, in solution in 250 cm$^3$ of water, are added over 1 hour at 10–15° C. and then the pH is adjusted to 1 with 6N hydrochloric acid. The slightly cloudy acidic solution is clarified by filtration through celite and rinsed with 300 cm$^3$ of water. A clear and colourless solution is obtained (1650 g).

Half of this solution (825 g) is charged to a 4 liter hydrogenator and then 65 g of 5% platinum on alumina comprising 50% of water, in suspension in 1200 cm$^3$ of water, are added. The hydrogenator is closed and purged with nitrogen and then with hydrogen. The reaction mass is heated to 35° C. with stirring and then the hydrogen pressure is raised to 4 bar. Hydrogenation is complete in 2 hours, the mass is cooled to 20° C., the device is purged with nitrogen and the reaction mixture is filtered through a sintered glass filter. The clear and colourless solution is brought to a pH of 7.9 by addition of N sodium hydroxide solution and the mixture precipitates. The suspension obtained is filtered through a sintered glass filter and the cake is washed with 3 times 200 cm$^3$ of water and dried at 40° C. at 1.33 kPa for 16 hours.

102.3 g of ((L)-α-aspartyl)-(L)-β-cyclohexylalaninamide are obtained with a yield of 89% with respect to the methyl ester of ((L)-α-aspartyl)-(L)-phenylalanine initially charged.

$^1$H NMR spectrum in d$_6$-DMSO, T=300° K., δ in ppm (300 MHz): between 0.70 and 1.80 (13H, m, 6 CH$_2$ and 1 CH), 2.28 and 2.52 (each 1H, respectively dd, J=9 and 16 Hz, and dd, J=5 and 16 Hz, CH$_2$CO), 3.75 (1H, q, J=5 and 9 Hz, NCH), 4.20 (1H, m, NCH), 6.95 and 7.60 (each 1H, s, CONH$_2$), 8.65 (1H, d, J=5 Hz, NH).

Infrared spectrum, KBr pellet, cm$^{-1}$: broad band from 3600 to 2000, bonded ν N—H, including ν NH$_3^+$ with maxima at approximately 3469+3365+3264+3180+3063, ν N—H of the amides and NH$_3^+$, 2922+2851 ν C—H of the cyclohexane, 2669+2605 primary amine salt, bands at approximately 1671 ν C═O of the primary amide, 1636 mainly ν C═O of the secondary amide, 1596 mainly ν$_{as}$ C═O of COO$^-$+deformation of NH$_3^+$, 1555 δ NH of the secondary amide, 1445 deformation of CH$_2$, 1396+1384 mainly ν$_s$ C═O of COO$^-$.

EXAMPLE 2

956 cm$^3$ of water are added to 239 g of the ammonium salt of ((L)-α-aspartyl)-(L)-phenylalaninamide obtained in Example 1. The mixture is maintained as is for 30 minutes and then stirred until dissolution is complete. A normal aqueous hydrochloric acid solution is added over 60 minutes to this solution, kept stirred at 15–25° C., until a pH of 6.0 is reached. The ((L)-α-aspartyl)-(L)-phenylalaninamide precipitates and a thick slurry is obtained, which slurry is filtered through a sintered glass filter and washed with 239 cm$^3$ of water. The cake is pulled dry thoroughly and then dried in an oven at 40±5° C. at 1.33 kPa for 12 hours. 176 g of ((L)-α-aspartyl)-(L)-phenylalaninamide are obtained with a yield of 78%.

$^1$H NMR spectrum with d$_6$-DMSO, T=300° K., δ in ppm (250 MHz): 2.3 and 2.5 (each 1H, m, COCH$_2$), 2.9 and 3.1 (each 1H, respectively dd, J=16 and 6Hz, and dd, J=16 and 3 Hz, CH$_2$Ph), 3.8 (1H, m, NCH), 4.5 (1H, m, NCH), 7.2 (1H, s, ½ CONH$_2$), 7.3 (5H, m, phenyl), 7.8 (1H, s, ½ CONH$_2$), 8.90 (1H, broad s, NH).

Infrared spectrum, KBr pellet, cm$^{-1}$: broad band from 3600 to 2000, bonded ν N—H with maxima at approximately 3387+3318+3210, ν N—H of the amides and 3031+2684+2628 ν NH$_3^+$, bands at approximately 1668 ν C═O of the primary amide, 1644 mainly ν C═O of the secondary amide, 1626 mainly δ N—H of the primary amide, 1550 mainly ν$_{as}$ C═O of COO$^-$+δ NH of the secondary amide, 1496 +1446 C═C monosubstituted benzene nucleus, 1394 ν$_s$ C═O of COO$^-$+δ NH$_4^+$+C—CONH$_2$, 1032 monosubstituted benzene nucleus, 748 γ C—H of the monosubstituted benzene nucleus, 704 cm$^{-1}$ deformation of the monosubstituted benzene nucleus, broad band from 800 to 400 with maximum at approximately 634, ω N—H.

EXAMPLE 3

2390 cm$^3$ of water are added to 239 g of the ammonium salt of ((L)-α-aspartyl)-(L)-phenylalaninamide obtained in Example 1. The mixture is maintained as is for 30 minutes and then stirred until dissolution is complete. 60 g of (L)-tartaric acid are added to this solution, kept stirred at 15–25° C. The mixture is kept stirred for 3 hours and then filtered through a sintered glass filter. The cake is washed with 239 cm$^3$ of water and then dried in an oven at 40±5° C. at 1.33 kPa for 12 hours. 205 g of((L)-α-aspartyl)-(L)-phenylalaninamide hemitartrate are obtained with a yield of 72%.

$^1$H NMR spectrum in d$_6$-DMSO, T=300° K., δ in ppm (250 MHz): 2.4 and 2.6 (each 1H, respectively dd, J =16 and 8 Hz, and dd, J =16 and 3 Hz, COCH$_2$), 2.9 and 3.1 (each 1H, respectively dd, J =16 and 10 Hz, and dd, J =16 and 3 Hz, CH$_2$Ph), 3.8 (1H, m, NCH), 4.0 (2H, s, ½ tartaric acid),4.5 (1H, m, NCH), 7.2 (1H, s, ½ CONH$_2$), 7.3 (5H, m, phenyl), 7.7 (1H, s, ½ CONH$_2$), 8.70 (1H, d, J=5 Hz, NH).

Infrared spectrum, KBr pellet, cm$^{-1}$: broad band from 3700 to 2200, bonded ν N—H, including ν NH$_3^+$, and O—H with maxima at approximately 3530+3495+3441+3390+3306+3190, ν O—H of the tartrate+ν N—H of the amides and NH$_3^+$+ν O—H of the acid, 2502 mainly acid O—H (and primary amide salt), bands at approximately 1728 (shoulder) ν C═O of the acid, 1668 ν C═O of the primary amide and ν C═O of the secondary amide, 1602 mainly ν$_{as}$ C═O of COO$^-$+NH deformations of the primary amide and of NH$_3^+$, 1532 δ NH of the secondary amide, 1497+1455 ν C═C monosubstituted benzene nucleus, 1474 deformation of the OH groups of the tartrate, 1395 ν$_s$ C═O of COO$^-$+ν C—CONH$_2$ of the amide, 1304 ν C—O of the acid, 1133+1081 ν C—OH of the tartrate, 756 γC—H of the monosubstituted benzene nucleus, 703 deformation of the monosubstituted benzene nucleus, 513 ω C—O of the COO$^-$ groups of the tartrate, broad band from 750 to 400 with maximum at approximately 616 ω N—H.

EXAMPLE 4

510 cm$^3$ of acetic acid are charged to a stirred 1 liter three-necked round-bottomed flask and then 102.3 g of ((L)-α-aspartyl)-(L)-cyclohexyl-alaninamide are added. After stirring for 30 minutes, a clear solution is obtained. 30 cm$^3$ of 12N hydrochloric acid are poured onto this solution over 15 minutes, the hydrochloride precipitates and a thick slurry is obtained, which slurry is filtered through a sintered glass filter and washed with 2 times 100 cm$^3$ of acetic acid. The cake is pulled dry thoroughly and then dried in an oven at 50° C. at 1.33 kPa for 16 hours.

113 g of ((L)-α-aspartyl)-(L)-β-cyclohexylalaninamide hydrochloride are obtained with an overall yield of 83% with respect to the methyl ester of ((L)-α-aspartyl)-(L)-phenylalaninc charged initially in Example 1.

$^1$H NMR spectrum in d$_6$-DMSO, T=300° K., δ in ppm (300 MHz): between 0.7 and 1.8 (13H, m, CH$_2$C$_6$H$_{11}$), 2.8 and 3.0 (each 1H, respectively dd, J=8 and 16 Hz, and dd, J=4 and 16 Hz, CH$_2$CO), 4.1 (1H, m, CH), 4.3 (1H, m, CH), 7.1 and 7.4 (each 1H, s, CONH$_2$), 8.7 (1H, d, J=8 Hz, NH).

Infrared spectrum, KBr pellet, cm$^{-1}$: broad band from 3700 to 2200 cm$^{-1}$, bonded ν N—H, including ν NH$_3^+$, and O—H with maxima at approximately 3432+3395+3362+3181+3046, ν N—H of the amides and NH$_3^+$+ν O—H of the acid, 2924+2852 ν C—H of the cyclohexane, 2698+2636 mainly acid O—H (and primary amine salt), bands at approximately 1736+1715 ν C═O of the acid, 1682 ν C═O of the primary amide, 1670 mainly ν C═O of the secondary amide, 1605+1586 mainly NH deformations of the primary amide and of NH3$^+$, 1556 δ NH of the secondary amide, 1450 deformation of CH$_2$, 1407 ν C—N of the amine+OH deformation of the acid, 1299 ν C—O of the acid, 1201 not attributed.

EXAMPLE 5

The ammonium salt of ((L)-α-aspartyl)-(L)-phenylalaninamide is prepared as described in Example 1 and is then employed directly under the following conditions:

1440 cm$^3$ of acetic acid arc charged to a 4 liter hydrogenator/cavitator and then 239 g of the ammonium salt of ((L)-α-aspartyl)-(L)-phenylalaninamide, in solution in 240 cm$^3$ of water, are added. 67 cm$^3$ of 12N hydrochloric acid are poured over 15 minutes into the solution obtained and then 130 g of 5% platinum on alumina comprising 50% of water are added. The hydrogenator is closed and purged with nitrogen and then with hydrogen. The reaction mass is heated to 55° C. with stirring and then the hydrogen pressure is raised to 4 bar. Hydrogenation is complete in 3 hours, the mass is cooled to 20° C., the device is purged with nitrogen and the reaction mixture is filtered through a sintered glass filter. The filtrate is charged to a 4 liter three-necked round-bottomed flask equipped with a stirrer and the hydrochloride is precipitated by addition of lo 67 cm$^3$ of 12N hydrochloric acid over 20 minutes. The slurry is filtered through a sintered glass filter and washed with 2 times 200 cm$^3$ of acetic acid. The cake is pulled dry thoroughly and then dried in an oven at 50° C. at 1.33 kPa for 16 hours.

114 g of ((L)-α-aspartyl)-(L)-δ-cyclohexylalaninamide hydrochloride are obtained with an overall yield of 84% with respect to the methyl ester of ((L)-α-aspartyl)-(L)-phenylalanine initially charged, the physical characteristics of which are identical to those described above in Example 4.

EXAMPLE 6

150 cm$^3$ of liquid ammonia are charged to a 2 liter jacketed reactor cooled by circulation at −40° C. and then 100 g of the methyl ester of ((L)-α-aspartyl)-(L)-phenylalanine are added over 15 minutes with stirring. A colourless solution is obtained, which solution is stirred for a further 10 hours at −40° C., and then 900 cm³ of 2-propanol are added over a time of one hour while allowing the temperature to rise to 20° C. The mixture crystallizes. It is kept stirred for a further 2 hours at 20° C. and then filtered through a sintered glass filter and washed twice with 200 cm³ of 2-propanol. 211 g of the wet ammonium salt of ((L)-α-aspartyl)-(L)-phenylalaninamide (comprising 54% weight/weight of 2-propanol) are obtained, which 211 g, dried in an oven at 35±5° C. at 1.33 kPa while flushing with nitrogen for 16 hours, result in 92.4 g of ((L)-α-aspartyl)-(L)-phenylalaninamide with a yield of 97%, the physical characteristics of which are identical to those of the product described in Example 2.

EXAMPLE 7

390 cm³ of acetic acid are charged to a 2 liter hydrogenator and then 65 g of ((L)-α-aspartyl)-(L)-phenylalaninamide, prepared as described in Example 6, are added. 36 cm³ of trifluoroacetic acid are poured over 5 minutes into the solution obtained and then 27 g of 5% platinum on alumina comprising 50% of water are added. The hydrogenator is closed and purged with nitrogen and then with hydrogen. The reaction mass is heated to 35° C. with stirring and then the hydrogen pressure is raised to 4 bar. Hydrogenation is complete in 1 hour, the mass is cooled to 20° C., the device is purged with nitrogen and the reaction mixture is filtered through a sintered glass filter and rinsed with 65 cm³ of acetic acid. The filtrate and the rinse liquor are charged to a 1 liter three-necked round-bottomed flask equipped with a stirrer and the hydrochloride is precipitated by addition, over 15 minutes, of 153 cm³ of a 1.5N solution of hydrochloric acid in acetic acid. The suspension is kept stirred at 20° C. for 2 hours, filtered through a sintered glass filter and washed twice with 65 cm³ of acetic acid. The cake is pulled dry thoroughly and dried in an oven at 50° C. at 1.33 kPa for 16 hours.

61 g of ((L)-α-aspartyl)-(L)-β-cyclohexylalaninamide hydrochloride are obtained with a yield of 81%, the physical characteristics of which are identical to those of the product described in Example 5.

One skilled in the art will readily appreciate that the present invention is well adapted to carry out the objects of the invention and obtain the ends and advantages mentioned, as well as those inherent therein. The compounds, compositions and methods described herein are presented as representative of the preferred embodiments, or intended to be exemplary and not intended as limitations on the scope of the present invention.

What is claimed is:
1. A method for preparing (α-aspartyl)-β-cyclohexylalaninamide, this method comprising, in a first stage, amidating an ester of aspartylphenylalanine of general formula:

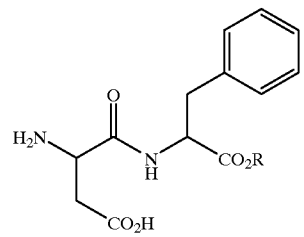

in which R is an alkyl radical comprising 1 to 4 carbon atoms, to give the ammonium salt of (α-aspartyl) phenylalaninamide of formula:

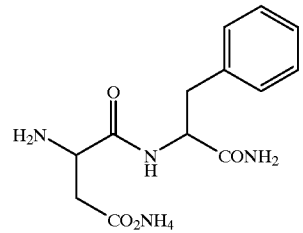

and then, in a second stage, catalytically hydrogenating the product obtained, optionally released beforehand from its salt, and then optionally converting the (α-aspartyl)-β-cyclohexylalaninamide thus obtained to an acid addition salt.

2. The method according to claim 1, wherein the product of the second stage is ((L)-α-aspartyl)-(L)-β-cyclohexylalaninamide or its acid addition salt.

3. A method for preparing (α-aspartyl) phenylalaninamide, its ammonium salt or its acid addition salt, this method comprising amidating an ester of aspartylphenylalanine of general formula:

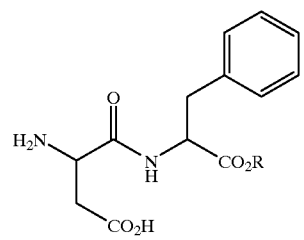

in which R is an alkyl radical comprising 1 to 4 carbon atoms, to give the ammonium salt of (α-aspartyl) phenylalaninamide of formula:

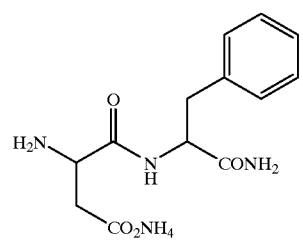

and then optionally releasing the product from its salt and optionally converting it to an acid addition salt.

4. The method according to claim 3, wherein ((L)-α-aspartyl)-(L)-phenyl-alanine is converted to ((L)-α- aspartyl)-(L)-phenylalaninamide, its ammonium salt or its acid addition salt.

5. The method according to claim 1 wherein said ester of aspartylphenylalanine is the methyl ester of (α-aspartyl) phenylalanine.

6. The method according to claim 3 wherein said ester of aspartylphenylalanine is the methyl ester of (α-aspartyl) phenylalanine.

7. The method according to claim 1 wherein the amidation reaction is carried out by reaction with liquid ammonia.

8. The method according to claim 3 wherein the amidation reaction is carried out by reaction with liquid ammonia.

\* \* \* \* \*